United States Patent
Yang et al.

(10) Patent No.: US 8,897,866 B2
(45) Date of Patent: Nov. 25, 2014

(54) MULTI-TOUCH APPROACH FOR ECG MEASUREMENT

(71) Applicants: Yu Yang, Bejing (CN); Xiaodong Du, Bejing (CN)

(72) Inventors: Yu Yang, Bejing (CN); Xiaodong Du, Bejing (CN)

(73) Assignee: Vales and Hills Biomedical Tech. Ltd., Beijing (CN)

( * ) Notice: Subject to any disclaimer, the term of this patent is extended or adjusted under 35 U.S.C. 154(b) by 0 days.

(21) Appl. No.: 13/926,735

(22) Filed: Jun. 25, 2013

(65) Prior Publication Data

US 2014/0148719 A1    May 29, 2014

(51) Int. Cl.
*A61B 5/04* (2006.01)
*A61B 5/0402* (2006.01)
*A61B 5/00* (2006.01)
*A61B 5/044* (2006.01)

(52) U.S. Cl.
CPC ........... *A61B 5/7475* (2013.01); *A61B 5/04023* (2013.01); *A61B 5/044* (2013.01)
USPC .......................................................... 600/523

(58) Field of Classification Search
None
See application file for complete search history.

(56) References Cited

U.S. PATENT DOCUMENTS

2011/0150291 A1* 6/2011 Jung ............................. 382/115

OTHER PUBLICATIONS

Saxon LA, Smith A, Doshi S, Dinsdale J, Albert D. iPhone Rhythm Strip—The Implications of Wireless and Ubiquitous Heart Rate Monitoring. J Am Coll Cardiol. 2012;59(13s1):E726.*
BIOPAC Systems, Inc. AS148—Automated ECG Analysis. 2006;pp. 1-7.*

* cited by examiner

*Primary Examiner* — Brian T Gedeon
*Assistant Examiner* — Ankit Tejani
(74) *Attorney, Agent, or Firm* — CBM Patent Consulting, LLC

(57) ABSTRACT

An ECG measurement approach for any multi-touch screens comprises the following steps: 1) display ECG on the screen; 2) use two fingers to touch the screen and the two touch points have two vertically projected points on the actual ECG waves; 3) draw the horizontal and vertical baselines to show the x interval in milliseconds and y interval in microvolt; 4) move any one or both of the two fingers touch points on the screen, the projected points and the horizontal/vertical baselines updated synchronously, as well as the measurements; 5) measure the different part of the ECG waves using this approach, including the wave top points, wave beginning and ending points. This approach can be used as a measurement tool to any graphs of functions over time displayed on the multi-touch screen, like EEG.

6 Claims, 2 Drawing Sheets

MULTI-TOUCH APPROACH FOR ECG MEASUREMENT

TECHNICAL FIELD OF THE INVENTION

This invention relates to the field of medical instrument involving an accurate and simple measurement for ECG (Electrocardiography) on multi-touch screens based on a multi-touch on a display screen.

BACKGROUND OF THE INVENTION

The terminologies are used in this invention as following:

Gesture: The finger touch actions on screen, like single point touch, touch slice, 2 points pinch (this is the one used in this invention), multi touches spin;

API: Application Programming Interface;

iOS: iOS is the operation system of Apple, run on Apple's mobile devices like iPhone, iPad;

The traditional ECG measurement is that doctors use the dividers to lock 2 points on ECG (on paper), and move the dividers on the standard ECG ruler to read the intervals between two points;

Alternativly,the ECG ruler (or other similar tool)is used to measure ECG directly on the display screens.

Disadvanges of the Traditional Methods:
① Obviously it is not to target the ECG which is diaplyed on screens;
② The operations are relatively complicated;
③ When measuring vertial interval, an additional ruler is needed to get the 2 points exactly on the same x coordinate.

On non-touch screen devices like PC screen, the measurement of ECG with PC mouse is utilized in the prior art which clicks on the initial point, drags mouse to the next point, then calculates.

The patent application (CN 200710092530.3) tiltled as "Approach of ECG measurement" discloses an ECG measurement approach which displays ECG waves on the screens, then determines the unit convert factor. After numberious of clickings on the wave top point, wave beginning and wave ending points with PC mouse, all clicked point coordinates are saved and calculated. The present invention discloses a method to use touch screen which replaces the clicks with PC mouse which does not use the screen touch feature for ECG measurement.

Neither the traditional measure approach using rulers, nor the mouse clicking and draging based approach, is user-friendly to yield accurate measurement for ECG.

In the prior art, there is no similar application on touch-screen devices as disclosed in the present invention, while the traditional mouse based approach can be not applied for the widely used touch screen devices in the field of ECG measurement. The present invention reveals a novel process of ECG measurement with a touch screen device.

SUMMARY OF THE INVENTION

The subject of the invention is to implement a novel process to measure ECG waves with a touch screen device by using multi-touch feature, which can yield horizontal interval and vertical interval between two touch points. This approach solves a long-desired problem which the ECG waves cannot be accurately measured with traditional approaches on display screens.

To implement the approach by using multi touches on screen comprises the following steps:

1) Collect ECG wave data through acquisition devices or by scanning ECG report and drawing on a display screen;
2) A user touches the screen using two fingers, and the horizontally projected point and the vertically projected point on the actual ECG waves are drawn. They are the actual measurement target points;
3) On the screen the following items are displayed: the horizontal and vertical baselines between the two target points, and the x interval (horizontal) in milliseconds and y interval (vertical) in microvolt between the two points are calculated;
4) To move the touched points on the screen and the projected target points, the baselines and the intervals can be updated on the screen;
5) To measure different positions of the ECG waves including the Wave top points, wave beginning and ending points by using this approach, and to analyze the acquired ECG measurement data from above steps to diagnose heart abnormalities or to study cardiology with a diagnosis software.

According to above steps of the measurement, the projected target points are based on the actual touch point coordinates on the screen, which is read with a gesture API provided by an operation system of a touch screen device.

According to the step 2 of above process of measurement of ECG, the way to get the target measurement points is that the assumed (x1, y1) and (x2, y2) are the 2 actual touch point coordinates, x1 and x2 are divided by pixelsPerPoint (pixels per point on screen), get n1 and n2 as the point index, respectively, through which we can read the voltage value on the y axis from the array voltage[ ]: v1 and v2 . Coordinates (n1, v1 ) and (n2, v2 ) are the target points projected on x axis and y axis. The two target points are drawn on the screen, we shall convert them into the pixels per point.

According to the step 3 of above process of measurement of ECG, the x interval and y interval are calculated as following:

X interval is $((n2-n1)/sample) \times 1000$ wherein the sample is sampling rate which is represented by points per second;

Y interval is: $v2-v1$.

According to the step 4 of above process of measurement of ECG, the measurement is synchronously performed while the finger touch points are moved.

This invention further discloses the specific steps to implement the approach on an iOS device. The API is UIPinchGestureRecognizer class in iOS. The two actual touch point coordinates on screen are generated by UIPinchGestureRecognizer:

numberOfTouches: Number of Touches;
locationOfTouch(int index): Coordinate of the touch index of index;

Following equations are used to calculate x1 and x2 wherrein x1 is a left point:

Int $x1$=self.touch1.$x$>=self.touch2.$x$?self.touch2.$x$: self.touch1.$x$;

int $x2$=self.touch1.$x$<=self.touch2.$x$?self.touch2.$x$: self.touch1.$x$;

The index of points are calculated with the ECG wave data (array):

int $n1$=Math.Floor($x1$/pixelsPerPoint);

int $n2$=Math.Floor($x2$/pixelsPerPoint);

The voltage values are calculated with the voltage[ ] array:

int v1=voltage[n1]

int v2=voltage[n2];

The following functions are used to draw the points and lines:
CGContextMoveToPoint: Set the line beginning point;
CGContextAddLineToPoint: Draw line to a point;
CGContextFillEllipseInRect: Draw point on a position;
CGContextStrokePath: Perform the drawing;

The major advantage of this invention is a very user-friendly method (touch screen using fingers and move) for users. The measurement of ECG waves is accurate and easy to perform.

The process of the present invention is applicable to other similar measurement, such as Brain Waves (electroencephalography), or other waves when the voltage is on y axis and time is on x axis.

DETAILED DESCRIPTION OF THE EMBODIMENTS

To make the invention more understandable, here is a detailed description for an example to explain how to implement the invention.

Figure 1:
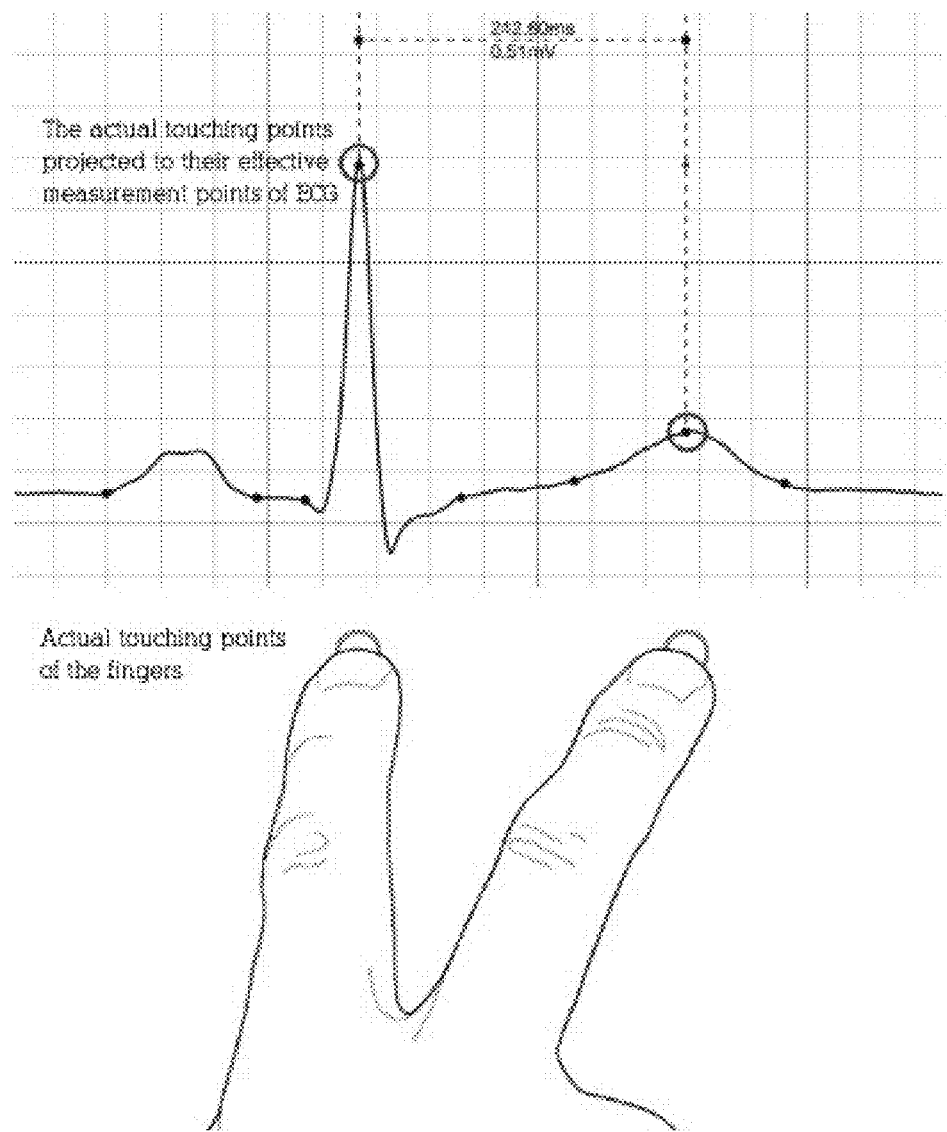
FIG. 1 is an example of the ECG measurement of present invention used for an ECG wave cycle.

FIG. 1 is an example using this invention approach to measure an ECG wave cycle. First, the ECG waves were shown on a display screen. Two fingers were used to touch the screen and the two touch points had two projected target points on the actual ECG waves. Horizontal and vertical baselines were drawn to indicate the x interval in milliseconds and y interval in microvolt. To move either one or both of the two finger touch points on the screen, the projected points and the horizontal/vertical baselines were updated synchronously, as well as the results of the measurement. The different positions, which include wave top points, wave beginning and ending points of the ECG waves, were measured with the approach of invention. The diagnosis for heart abnormalities was performed based on the results of measurements.

Implementation Details:

Multi-touch screen devices (such as iPad) can provide a series of gesture API, and the API application is able to acquire the finger touch data (coordinates) and the event when the finger touches and slices.

Inputs are:

Assumed (x1, y1) and (x2, y2) are the two actual touch point coordinates, and the following parameters are pre-defined:
Sample: sampling points per second,
Points: the duration of the target ECG wave in points,
Voltage[ ]: the array of voltage value of each points on the wave,
pixelsPerPoint: the pixel number on screen per point occupies.

Program Process:

x1 and x2 were divided by pixelsPerPoint (pixels per point on screen) which yielded n1 and n2 as the point index, respectively, through which we could read the voltage values as v1 and v2 on the y axis from the array voltage[ ]. Coordinates (n1, v1 ) and (n2, v2 ) were the target points projected on x axis and y axis.

The two target points, which were converted into the pixels per point, were drawn on the screen.

Outputs were:

The x interval in milliseconds and y interval in microvolt were calculated by $$x=((n2-n1)/\text{sample})\times 1000,$$

$$y=v2-v1.$$

When users moved the touch figures (one or both) on the screen, the calculation was performed synchronously and the results of measurement were shown in real time. The approach of present invention can potentially improve the measurement efficiency and accuracy.

Figure 2:
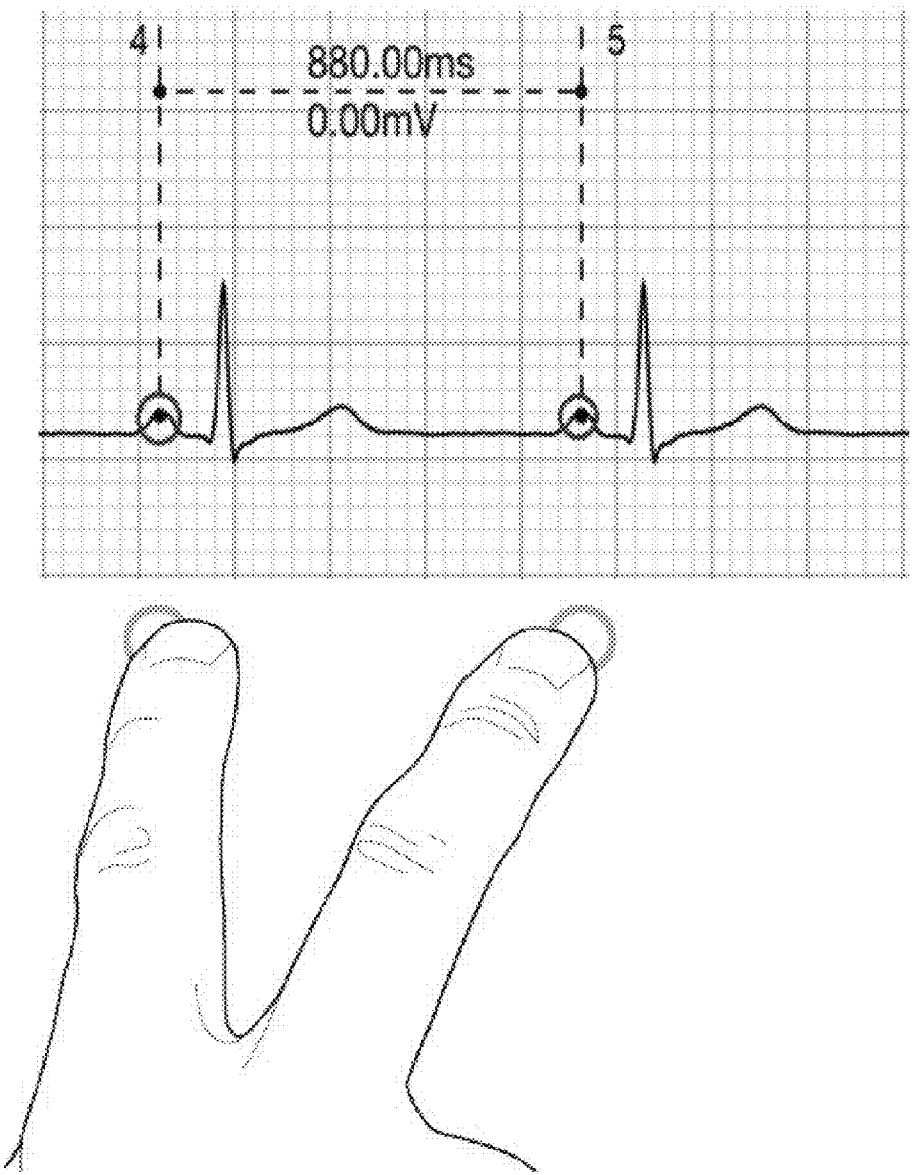
FIG. 2 is an example of the ECG measurement of present invention used for multiple ECG waves.

FIG. 2 is an example of measurement of ECG wave among multiple ECG waves.

EXAMPLE

The iOS was taken as an eample, the following was a detailed description to implement the approach of present invention.

iOS provides a series of gesture API to capture the finger touches and movement events, the most of API being used is UIPinchGestureRecognizer class. UIPinchGestureRecognizer is a sub class that targets to pinch gestures on the screen. When two points were touched, an instance of UIPinchGestureRecognizer class was created, and the two actual touch point coordinates on screen were generated by this instance:

numberOfTouches: Number of Touches;

locationOfTouch(int index): Coordinate of the touch index of index.

Followings were equations for calculating x1 and x2 (x1 is the relative left point):

Int $x1$=self.touch1.$x$>=self.touch2.$x$?self.touch2.$x$: self.touch1.$x$;

int $x2$=self.touch1.$x$<=self.touch2.$x$?self.touch2.$x$: self.touch1.$x$.

The index of the point was calculated with the ECG wave data (array):

int $n1$=Math.Floor($x1$/pixelsPerPoint);

int $n2$=Math.Floor($x2$/pixelsPerPoint).

The voltage values were calculated with the voltage[ ] array:

int v1=voltage[n1];

int v2=voltage[n2].

The following functions were used to draw the points and lines:
CGContextMoveToPoint: Set the line beginning point;
CGContextAddLineToPoint: Draw line to a point;
CGContextFillEllipseInRect: Draw point on a position;
CGContextStrokePath: Perform the drawing.

Above are examples to explain how to implement the invention, which helps to illustrate the subject of the invention, the solution and advantages thereof. An important point to declare is that above description is only an example of the invention, not include all about the invention. And any technologies derived from the invention, equivalent replacements and improvements are all covered in the claimed range of the invention.

The invention claimed is:

1. A process for measuring electrocardiography (ECG) based on multi-point touch on a display screen comprising the following steps:
   a. Collect ECG data with an acquisition device, or by scanning ECG report, or by drawing on the screen;
   b. Two fingers touch two points simultaneously on the screen, which projects two target points on waves of the ECG which is loaded on the screen;
   c. Generate a horizontal baseline and a vertical baseline between the two target points, and calculate the horizontal interval (x) in milliseconds and vertical interval (y) in microvolt between the two target points;
   d. Move the fingers and project two new target points, update new baselines and new intervals between the two new target points;
   e. Repeat steps b. c. and d. to measure the intervals for different positions of the waves of the ECG including wave top point, wave beginning point and wave ending point;
   f. Analyze acquired data from above steps to diagnose heart abnormalities or to study cardiology
   wherein the two touch point coordinates are designated as (x1, y1) and (x2, y2); the x1 and x2 divided by pixelsPerPoint results in point index n1 and n2, respectively, through which the voltage values on y axis from voltage[ ]array are v1 and v2, which yields two target point coordinates designated as (n1, v1) and (n2, v2), wherein pixelsPerPoint represents pixels per point on screen; then drawing the two target points on the screen based on the pixels per point.

2. The process according to claim 1, wherein the projected target points are generated by two actual touch point coordinates on the screen which is revealed by a gesture application program interface (API) provided by an operation system of a touch screen device.

3. The process according to claim 1, wherein the x interval and y interval are calculated by which the x interval is ((n2−n1)/sample)×1000, wherein the sample is a sampling rate that is represented by the points per second; y interval is v2 −v1.

4. The process according to claim 1, wherein the measurement of ECG is synchronously performed as one or two fingers are moved on the screen.

5. The process according to claim 2 wherein the operating system of the touch screen device provides the gesture API that is an UIPinchGestureRecognizer which generates the following parameters when the fingers touch the screen:
   numberOfTouches : Number of Touches,
   locationOfTouch(int index): Coordinate of the touch index of index;
   calculates the x1 and x2 with the following equations wherein x1 represents the left touch point:

int $x1$=self.touch1.$x$ >=self.touch2.$x$ ? self.touch2.$x$: self.touch1.$x$, int $x2$=self.touch1.$x$ <=self.touch2.$x$ ? self.touch2.$x$: self.touch1.$x$;

calculates the point index of two touches on the ECG waves with the pixels per point:

int $n1$=Math.Floor($x1$/pixelsPerPoint), int $n2$ =Math.Floor($x2$/pixelsPerPoint);

reads voltage values from the voltage[ ] array of ECG:

int v1=voltage[n1], int v2=voltage[n2];

and draws the points and lines on the screen with the following functions:
   CGContextMoveToPoint: Set the line beginning point,
   CGContextAddLineToPoint: Draw line to a point,
   CGContextFillEllipseInRect: Draw point on a position,
   CGContextStrokePathPerform the drawing.

6. The process according to claim 1, wherein diagnostic software is used for the diagnosis of heart abnormalities based on the acquired data.

* * * * *